United States Patent [19]

Dannan

[11] Patent Number: 5,441,059

[45] Date of Patent: Aug. 15, 1995

[54] METHOD OF MINIMALLY INVASIVE SURGERY

[76] Inventor: Patrick A. Dannan, 446 Lynwood Forest, Manchester, Mo. 63021

[21] Appl. No.: 191,026

[22] Filed: Feb. 2, 1994

[51] Int. Cl.⁶ .............................................. A61B 19/00
[52] U.S. Cl. .......................................... 128/898; 606/1
[58] Field of Search ................................ 606/205–211, 606/1, 138–147; 128/898

[56] References Cited

U.S. PATENT DOCUMENTS

| | | | |
|---|---|---|---|
| 3,918,439 | 11/1975 | Zimmer | 128/7 |
| 4,798,193 | 1/1989 | Giesy et al. | 128/7 |
| 4,921,479 | 5/1990 | Grayzel | 604/53 |
| 4,981,482 | 1/1991 | Ichikawa | 606/108 |
| 5,131,379 | 7/1992 | Sewell, Jr. | 128/4 |
| 5,141,519 | 8/1992 | Smith et al. | 606/205 |
| 5,312,391 | 5/1994 | Wilk | 606/1 |
| 5,336,238 | 8/1994 | Holmes et al. | 606/205 |

Primary Examiner—Stephen C. Pellegrino
Assistant Examiner—Glenn Dawson
Attorney, Agent, or Firm—Armstrong, Teasdale, Schlafly & Davis

[57] ABSTRACT

A method of conducting minimally invasive surgery includes the steps of making a primary incision; importing at least one surgical instrument head through the primary incision; making at least one secondary incision, smaller than the primary incision and the cross-section of the surgical instrument head, for a handle; extending the distal end of the handle through each secondary incision; attaching one of the surgical instrument heads to the distal end of the handle; manipulating the surgical instrument head with the handle to which it is attached; detaching the surgical instrument head from the handle; removing the surgical instrument head through the primary incision; and withdrawing the distal end of the handle from the secondary incision.

20 Claims, 8 Drawing Sheets

METHOD OF MINIMALLY INVASIVE SURGERY

BACKGROUND AND SUMMARY OF THE INVENTION

This invention relates to a method of performing minimally invasive surgery, and to surgical instruments adapted for use performing such surgery.

Laparoscopic surgical techniques have greatly reduced the trauma and recovery time associated with many kinds of surgery. In a typical laparoscopic surgery, a small incision is made at the umbilicus for the introduction of a small video camera. The abdomen is inflated with carbon dioxide. One or more punctures are made through the abdomen wall for the introduction of surgical instruments through the abdomen wall. Although design refinements have made these instruments compact, the punctures required are still relatively large, ranging from about 15 to about 100 french (about 5 to about 30 mm or about 0.197 to about 1.179 inches). While relatively small, these punctures are traumatic to the patient, and take considerable time to heal properly. In view of the size of laparoscopic instruments heretofore available, laparoscopic techniques generally cannot be used for many types of thoracic surgery because the instruments cannot pass through the small inter-rib spacing.

Generally the method of conducting minimally invasive surgery according to the present invention comprises the steps of: making a primary incision; importing at least one surgical instrument head through the primary incision; making at least one secondary incision, smaller than the primary incision and smaller than the cross-section of the surgical instrument head, for the introduction of a handle into the body; extending the distal end of the handle through the secondary incision; and attaching one of the surgical instrument heads to the distal end of the handle inside the body. The surgical instrument head is then manipulated inside the body by the handle to which it is attached. The surgical instrument head is then detached from the handle, and eventually removed from the body through the primary incision. The distal end of the handle is simply withdrawn from the secondary incision.

The handle can provide mechanical, pneumatic, or hydraulic pressure or electric or optical power to the surgical instrument head mounted on its distal end. Of course, more than one surgical instrument head can be imported through the primary incision, and multiple handles can be used so that more than one surgical instrument head can be used at a time. Moreover, providing multiple surgical instrument heads allows the surgical instrument heads to be changed as the surgery progresses, for example allowing a cutting surgical instrument head to be replaced with a suturing surgical instrument head.

The primary incision is preferably made through the umbilicus, but could also be made through the super pubic region or other discrete entry site on the body to minimize visible scarring. Because the secondary incisions do not have to pass the surgical instrument heads, the secondary incisions can be made very small, minimizing injury and pain to the patient, and subsequent visible scarring. Also, because of their small size, the secondary incisions can be made through the patient's rib cage, between the ribs, for conducting thoracic surgical procedures, allowing the surgical instrument heads to be manipulated with handles extending between the patient's ribs. If desired, the secondary incisions could be made from the inside out, by using the surgical instrument heads imported through the primary incision.

According to the method of this invention, surgery can be conducted with a single primary incision. The secondary incisions for the handles can be of the size of medium size needles. Thus the trauma and discomfort to the patient is substantially reduced, and the recovery time is shortened. Patients will suffer less post-operative pain, and will be able to return home sooner. Moreover, since the primary incision can be located in the umbilicus, or other discrete site there will be little if any visible scarring.

These and other features and advantages will be in part apparent, and in part pointed out hereinafter.

BRIEF DESCRIPTION OF THE DRAWINGS

Corresponding reference numerals indicate corresponding parts throughout the several views of the drawings.

DETAILED DESCRIPTION OF THE PREFERRED EMBODIMENTS

Figure 1:
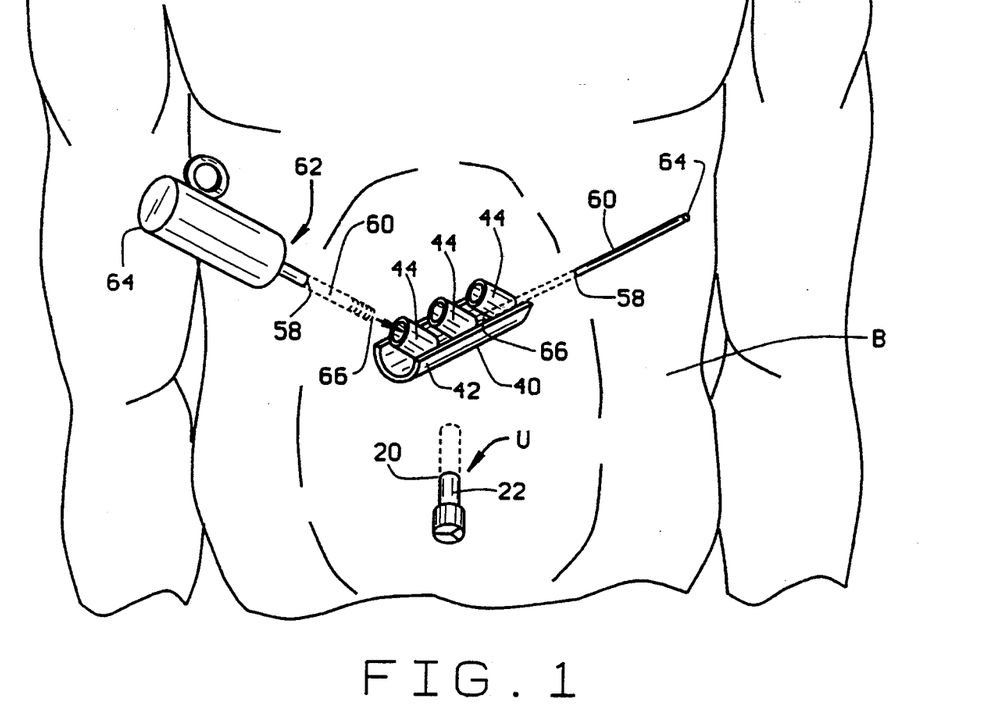
FIG. 1 is a top plan view of a patient undergoing a surgical procedure according to the principles of a first embodiment of this invention.
Figure 2:
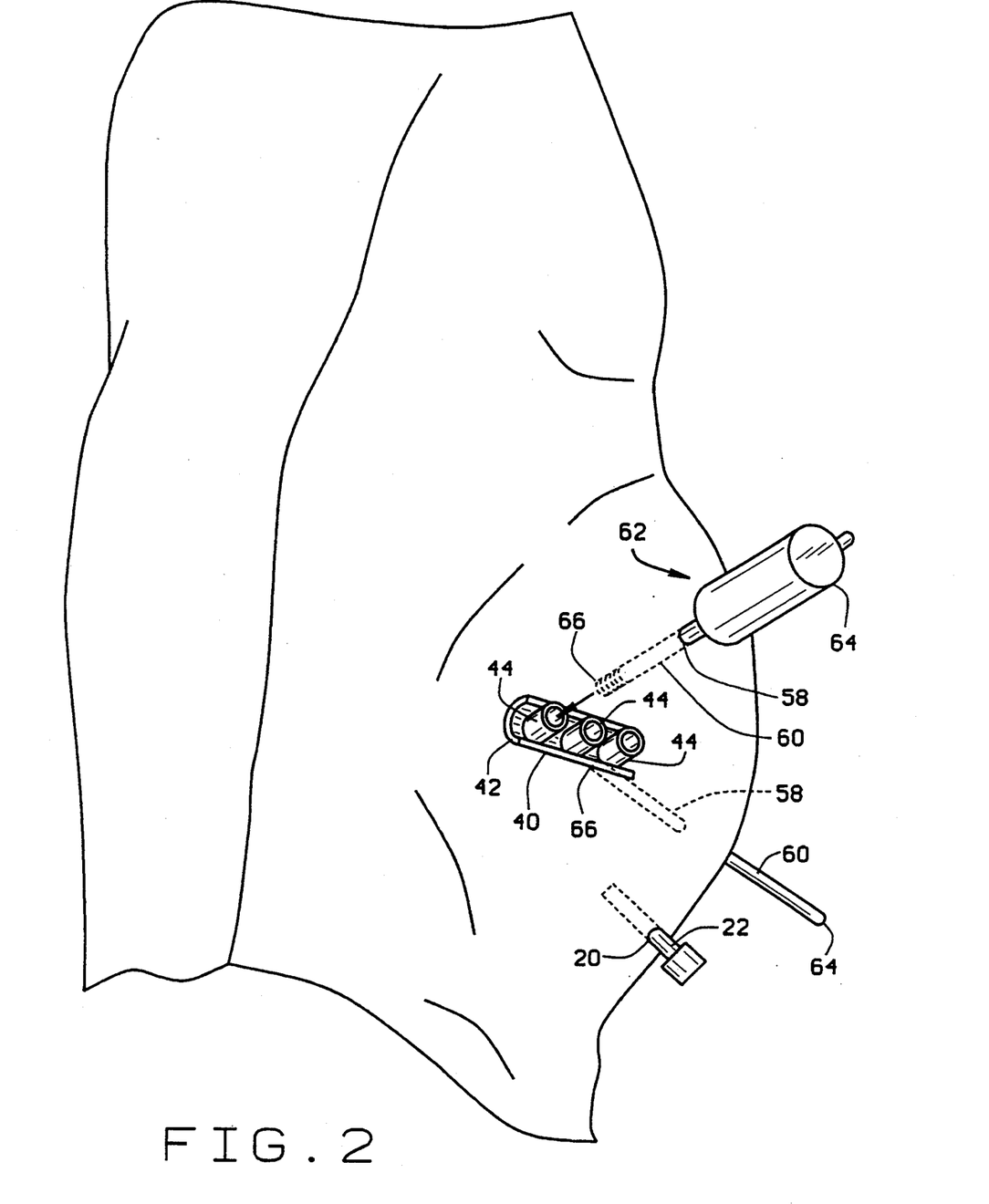
FIG. 2 is a side elevation view of the patient undergoing the surgical procedure according to the principles of the first embodiment of this invention.

A first embodiment of a method of minimally invasive surgery according to this invention is illustrated in FIGS. 1 and 2. According to this method, a primary incision is 20 made in the patient's body B, preferably through the umbilicus U, and a cannula 22 is inserted through the incision. This is conveniently done in one step with a conventional trocar sheathed in the cannula. The patient's abdomen is then inflated with carbon dioxide to provide a work space. As in a conventional laparoscopic surgery, the cannula 22 through the primary incision 20 provides a sealed access to the work space in the patient's abdomen for one or more cameras so that the surgeon can view the surgery. However, according to the method of this invention, the cannula through the primary incision 20 also provides access to the interior of the patient's body for the importation of one or more surgical instrument heads 24. It is also possible to import light sources to provide lighting for the surgical cameras, and to permit the use of smaller cameras without their own light sources through the secondary incisions described below.

Figure 11:
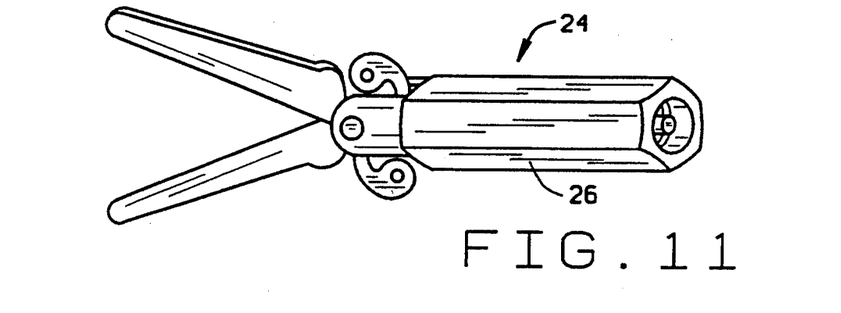
FIG. 11 is a perspective view of a double action straight scissors surgical instrument head constructed according to the principles of this invention.
Figure 12:
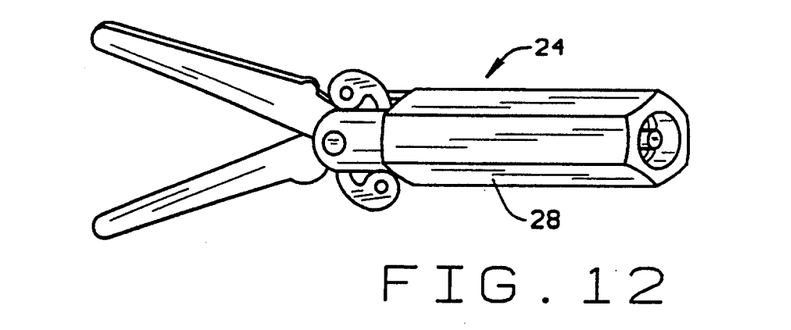
FIG. 12 is a perspective view of a double action curved scissors surgical instrument head constructed according to the principles of this invention.
Figure 13:
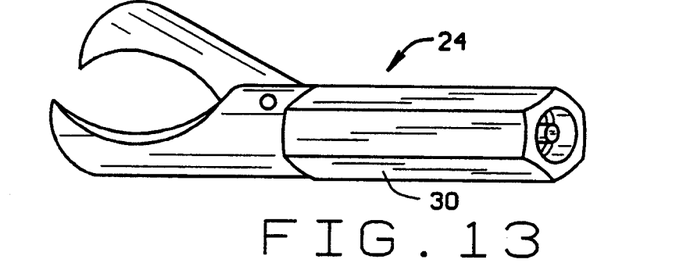
FIG. 13 is a perspective view of a hook scissors surgical instrument head constructed according to the principles of this invention.
Figures 14, 15:
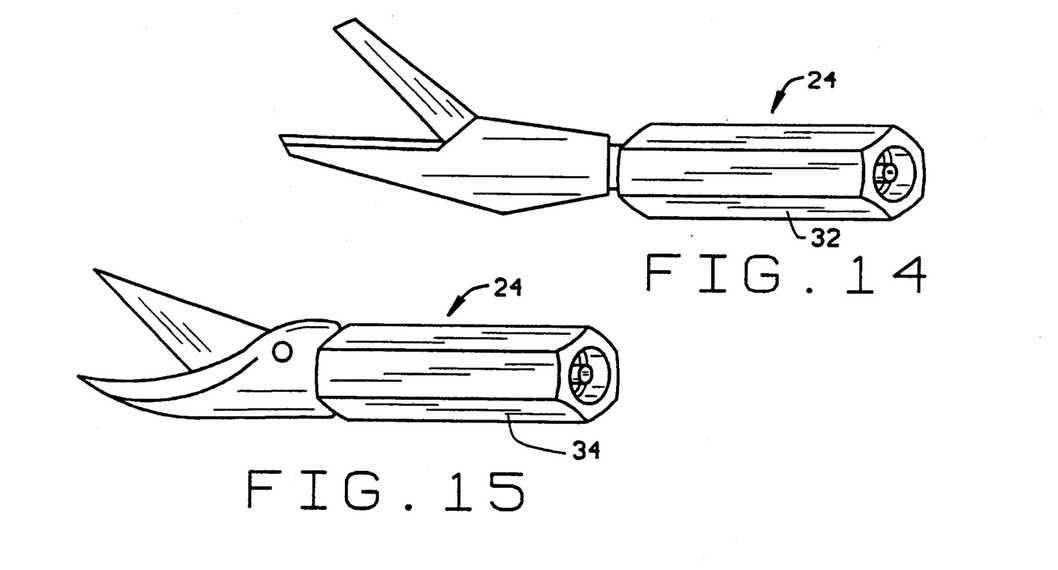
FIG. 14 is a perspective view of a large operating scissors instrument head constructed according to the principles of this invention.
FIG. 15 is a perspective view of a micro-dissecting scissors instrument head constructed according to the principles of this invention.
Figure 16:
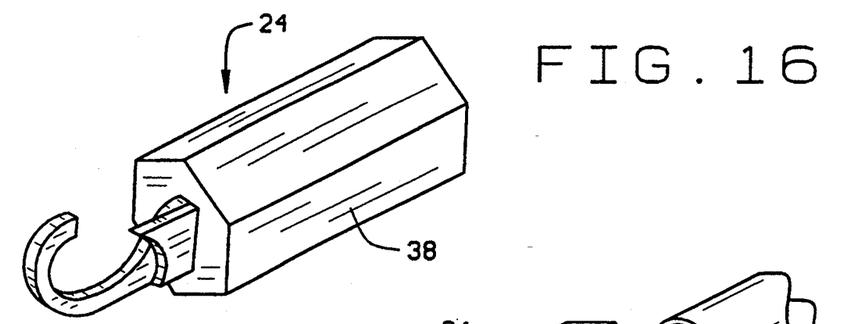
FIG. 16 is a perspective view of a J-hook tip with knife surgical instrument head constructed according to the principles of this invention.
Figure 17:
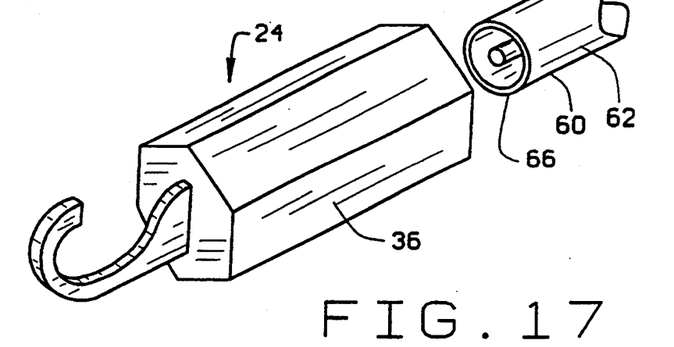
FIG. 17 is a perspective view of a cautery surgical instrument head constructed according to the principles of this invention.

Examples of possible surgical instrument heads 24 are shown in FIGS. 11-17. FIG. 11 illustrates a double action straight scissors surgical instrument head 26, that can be used for making straight cuts. FIG. 12 illustrates a double action curved scissors surgical instrument head 28, that can be used, for example, to make curved cuts. FIG. 13 illustrates a hook scissors surgical instrument head 30, that can be used, for example, to cut small vessels. FIG. 14 illustrates a large operating scissors instrument head 32, that can be used, for example, to make large cuts. FIG. 15 illustrates a micro-dissecting scissors instrument head 34, that can be used, for example, to make small cuts. FIG. 16 illustrates a J-hook tip with knife surgical instrument head 36, that can be used, for example, to hook and cut small vessels. FIG. 17 illustrates a cautery surgical instrument head 38, that can be used, for example, to cauterize broken blood vessels in cut tissues.

According to the first embodiment of this invention, the surgical instrument heads 24 can be stored in a tray 40 to facilitate their introduction through the cannula 22 that extends through the primary incisions 20, and to provide safe storage of the surgical instrument heads while they are inside of the patient's body B. As shown in FIGS. 1 and 2, the tray 40 can comprise a semi-cylindrical base 42, with a plurality of tool-holding sleeves 44 pivotally attached at one end to the base so that the sleeves can be pivoted into the base so that the tray assumes a generally circular cross-section to pass through the cannula 22. Once the tray 40 is inside of the patient's body, the sleeves 44 can be pivoted up from the base 42 to allow access to the surgical instrument heads 24 in the sleeves.

Figure 3:
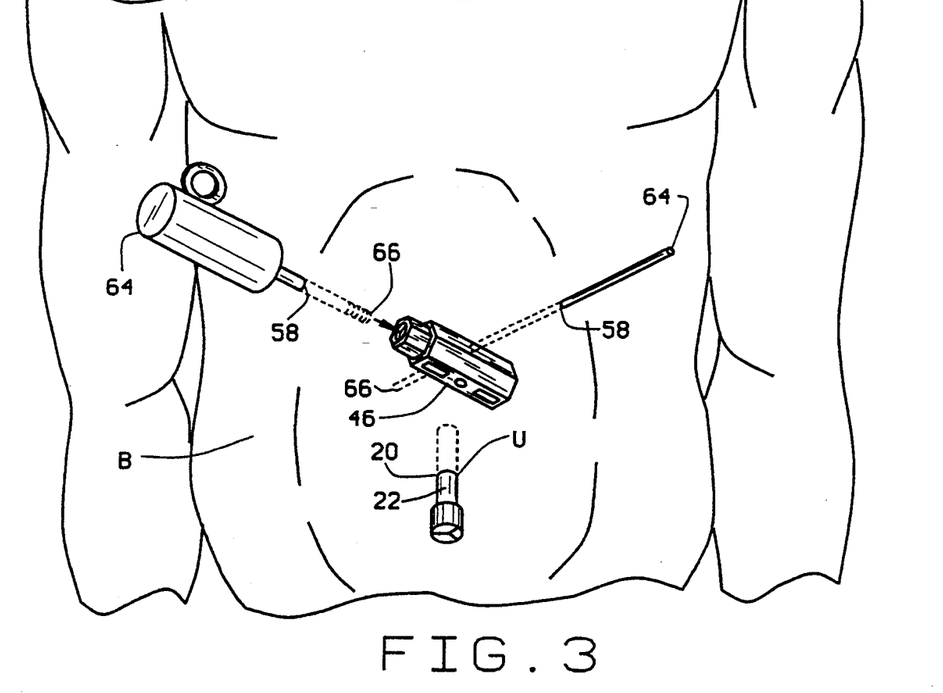
FIG. 3 is a top plan view of a patient undergoing a surgical procedure according to the principles of a second embodiment of this invention.
Figure 4:
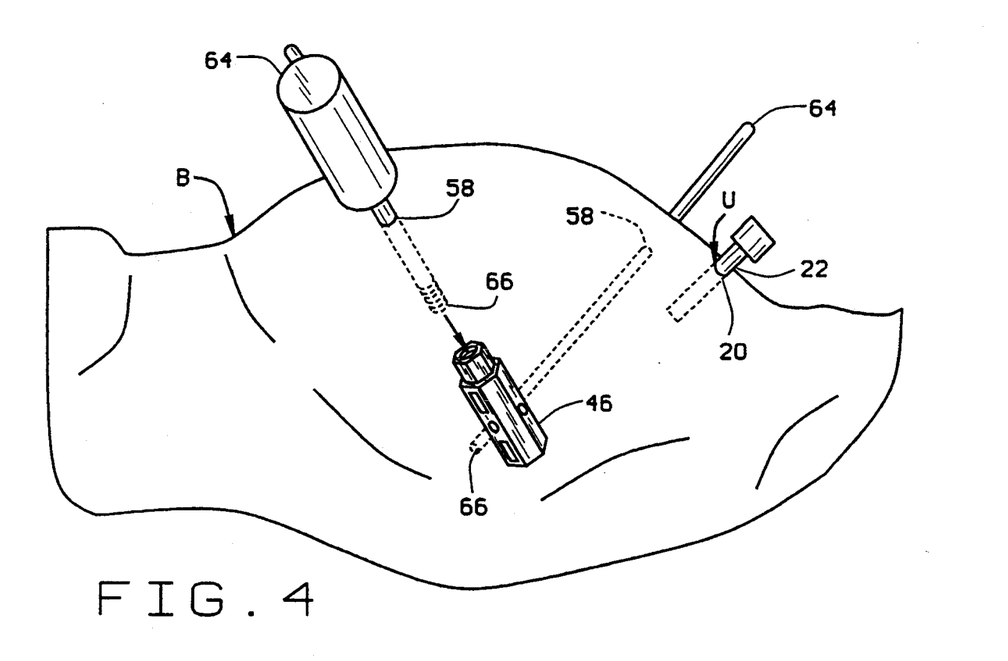
FIG. 4 is a side elevation view of the patient underground the surgical procedure according to the principles of the second embodiment of this invention.
Figure 9:
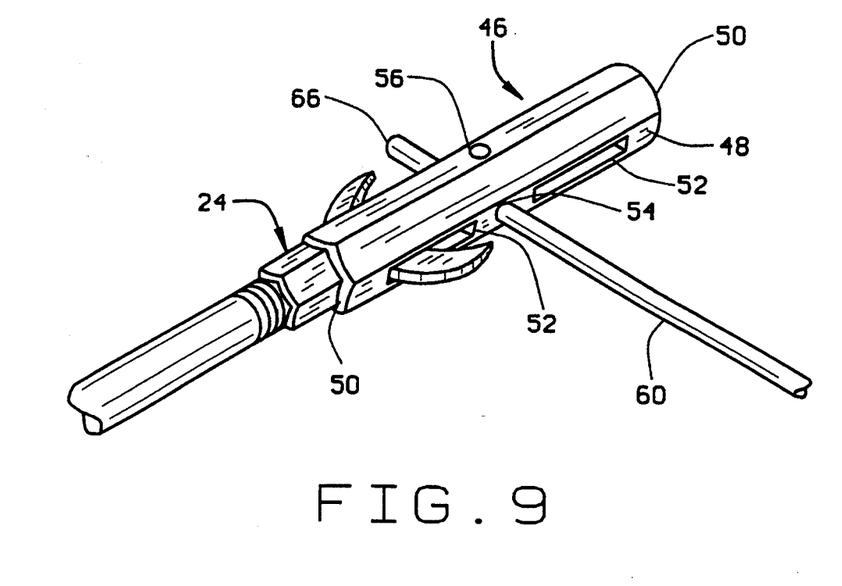
FIG. 9 is a perspective view of a surgical instrument head holder, illustrating the attachment of a handle to a surgical instrument head.
Figure 10:
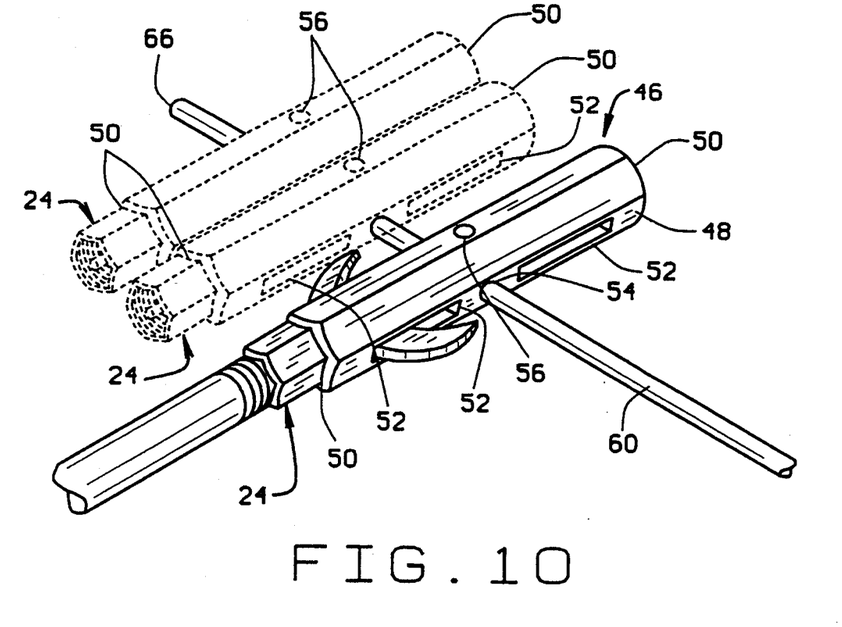
FIG. 10 is a perspective view of several surgical instrument head holders on a handle.

As shown in FIGS. 3 and 4, according to a second embodiment of this invention, instead of a tray 40, the surgical instrument heads 24 can be held and transported in tool holder 46. As shown in FIGS. 9 and 10, the tool holder 46 comprises an elongate housing 48 with a socket 50 in each end for receiving one of the surgical instrument heads 24. The housing 48 has a cross-section that is sized and shaped to pass through the cannula 22 that extends through the primary incision 20. The sockets 50 preferably have a non-circular cross-section (Such as a hexagon or other polygon), or other means, to securely hold the surgical instrument heads 24 against rotation so that a handle can be attached to and detached from a surgical instrument head held in the socket. Each of the sockets 50 preferably has a window 52 therein so that the proper operation of the surgical instrument head upon attachment of a handle can be confirmed by observation of the movement of the surgical instrument head through the window, before the surgical instrument head is removed from the socket. There are preferably two offset support holes 54 and 56 extending transversely through the housing 48 so that a handle can be attached to the tool holder 46 to manipulate the tool holder inside the patient's body B, and support the tool holder above the patient's organs.

Figure 5:
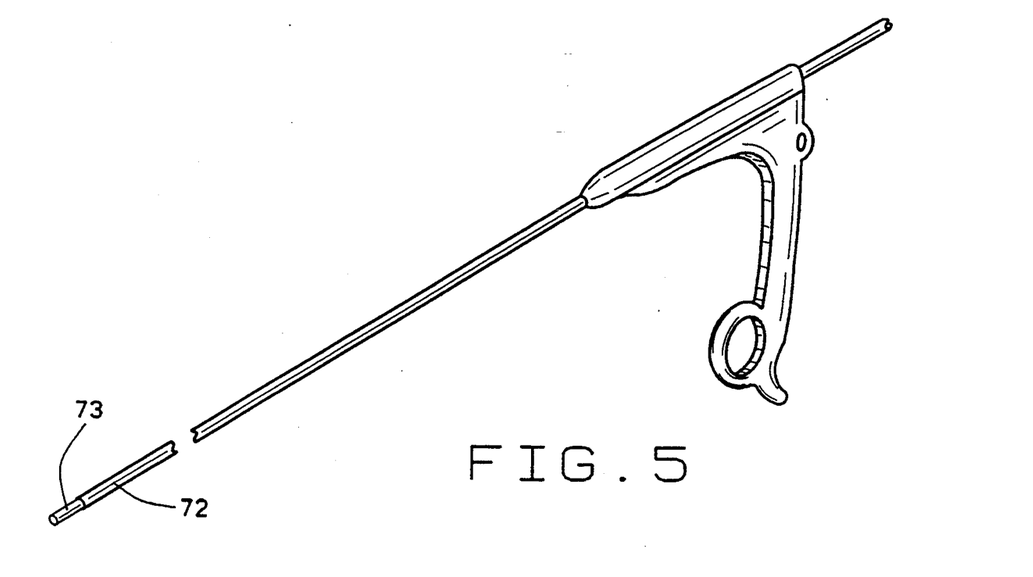
FIG. 5 is a perspective View of a trocar and sheath for making the secondary incisions according to the principles of this invention.
Figure 6:
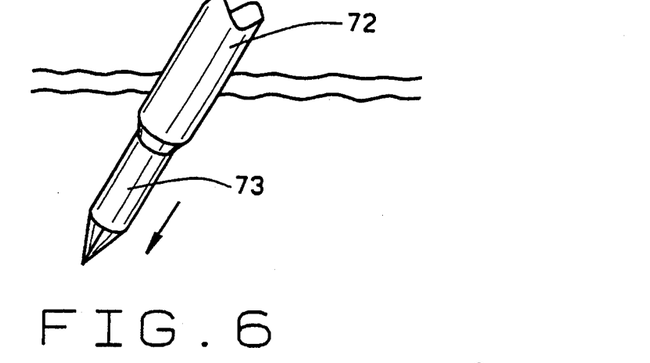
FIG. 6 is a perspective view of trocar and sheath shown piercing the skin to make a Secondary incision for the instruction of the handle.
Figure 7:
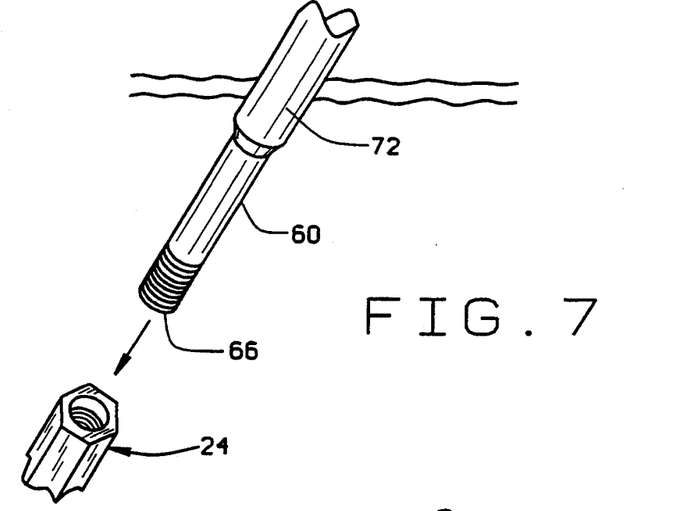
FIG. 7 is a perspective view of the handle inserted through the sheath and being aligned with a surgical instrument head.

At least one secondary incision 58 is made in the patient's body B. The secondary incisions 58 are smaller than the primary incision 20, and they are smaller than the cross-section of the surgical instrument heads 24. The secondary incisions 58 are preferably about the size of a medium gauge needle, about 6 to about 7 french (about 2.8 to about 3.2 mm or about 0.11 to about 0.13 inches), and permit the passage of the shaft 60 of a handle 62 into the work space inside the patient's body B. Because of their small size, the secondary incisions 58 can be made wherever convenient to best position a handle to operate the surgical instrument heads. Moreover, because of the small size of the secondary incisions 58, the secondary incisions can be placed closely together, allowing the surgeon to concentrate instruments in critical areas, even in an area susceptible to scarring. The handles 62 each have a proximal end 64 and a distal end 66. The proximal end 64 preferably includes a hand grip 68, and may include one or more controls 70, as described in more detail below. The distal end 66 of the handle 62 is inserted through one of the secondary incisions 58, and into the patient's body B. The shaft 60 of the handle 62 is preferably contained within a sheath 72 that protects the tissue surrounding the secondary incision 58 from the movement of the handle 62. Alternatively, the shaft could be coated with insulating material. Although, in some cases, neither a sheath nor insulating materials will be necessary. The sheath 72 can be made flexible, and thus can accommodate curved or bent handles that give the surgeon better leverage. The puncture 58 is preferably made with, and the sheath 72 is preferably installed with a pointed tip trocar 73, shown in FIG. 5. Alternatively, the distal end 66 of the handle 62 may be pointed, so that the handle 62 and the sheath 72 can be simultaneously inserted through the patient's body B, the pointed distal end 66 of the handle, forming the secondary incision 58 and allowing the shaft 60 of the handle and the sheath 72 to be introduced through the wall of the body. Alternatively, the distal end 66 of the handle 62 can be blunt, and the handle could be connected to an ultrasonic/high frequency driver which vibrates the blunt end of the handle to penetrate the body forming a small puncture around the handle.

After the distal end 66 of the handle 62 is inside the patient's body B, one of the surgical instrument heads 24 is attached to the distal end, inside of the patient's body. The distal end 66 of the handle 62 is manipulated to one of the sleeves 44 of tray 40, or one of the sockets 50 in the tool holder 46. One of the surgical instrument heads 24 is then releasably attached to the distal end 66 of the handle 62. The means for attaching the surgical instrument head 24 to the distal end 66 of the handle 62 is preferably a mating sets of threads; but some other suitable attaching mechanism could be used, for example a bayonet-type locking mechanism or detents.

Because of their small Size, the secondary incisions 58 can be made wherever is convenient for the surgeon, including between the patient's ribs in order to facilitate thoracic surgery. The handles 62 can extend between the ribs, giving the surgeon access to the thoracic cavity.

Figure 8:
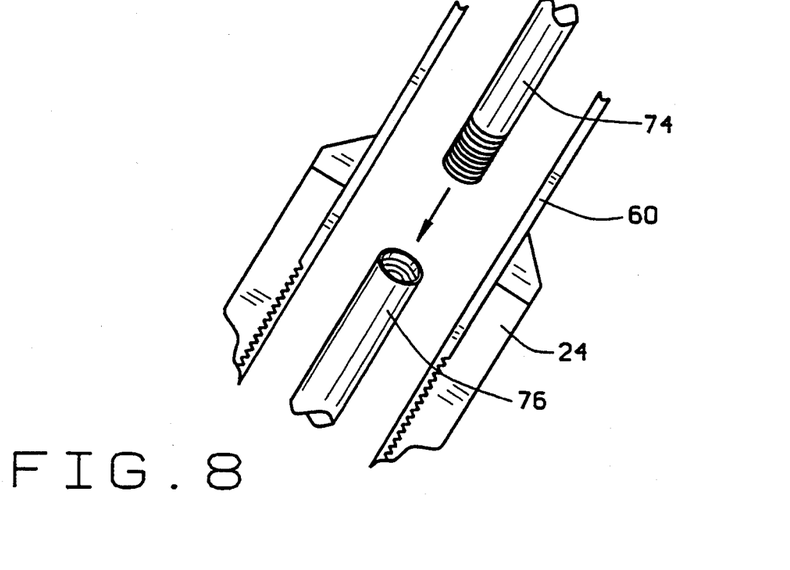
FIG. 8 is a longitudinal cross-sectional view of the showing the internal connection of the actuator in the handle with the surgical instrument head.

The handles 62 can provide mechanical, hydraulic, pneumatic, ultrasonic, electric or optical power to the surgical instrument heads 24. For example the shaft 60 of the handle 62 can be hollow, and can have an actuator 74 extending longitudinally therethrough, which can be mechanically actuated to operate the surgical instrument heads 24, for example closing the jaws of the scissors 30, 32, or 34 or the jaws of a gripper. As shown in FIG. 8, the actuator 74 preferably has its own fastening mechanism, such as threads, detents, or other suitable fasteners for engaging the movable element 76 on the surgical instrument head 24, to transmit the motion of the actuator 74 inside the shaft 60 of the handle 62, to the surgical instrument head. Pneumatic or hydraulic power can aid the surgeon in actuating the instrument heads. Ultrasonic power can also be provided to the shaft 60 of the handle 62, for example to operate scissors through vibration, or to ultrasonically cut or coagulate, as is known in the art. Of course more than one actuator 74 can be provided in handle 62, and these multiple actuators can be actuated to operate the double acting scissors 26 or 28. Alternatively, an insulated conductor 78 can be provided in the handle 62, for example to provide electrical energy to cautery head 38, in either a monopolar or bipolar configuration. In this case the insulated conductor 78 has means such as threads for mechanically engaging and electrically connecting with an electrical element on the cautery head 38 to electrically cauterize the tissue contacted by the head.

The handles 62 allow the surgical instrument heads 24 to be manipulated inside the patient's body B, so that the surgeon can perform the surgery. Because of their relatively thin size, the surgeon can bend the handles 62 either before insertion, or during the surgery, to achieve the desired control and positioning of the surgical instrument heads 24. The surgical instrument heads can also be made with a bend or curve to provide the surgeon with better leverage or control. This has not been possible with conventional laparoscopic techniques, where the entire instrument must pass through a straight cannula.

Figure 18:
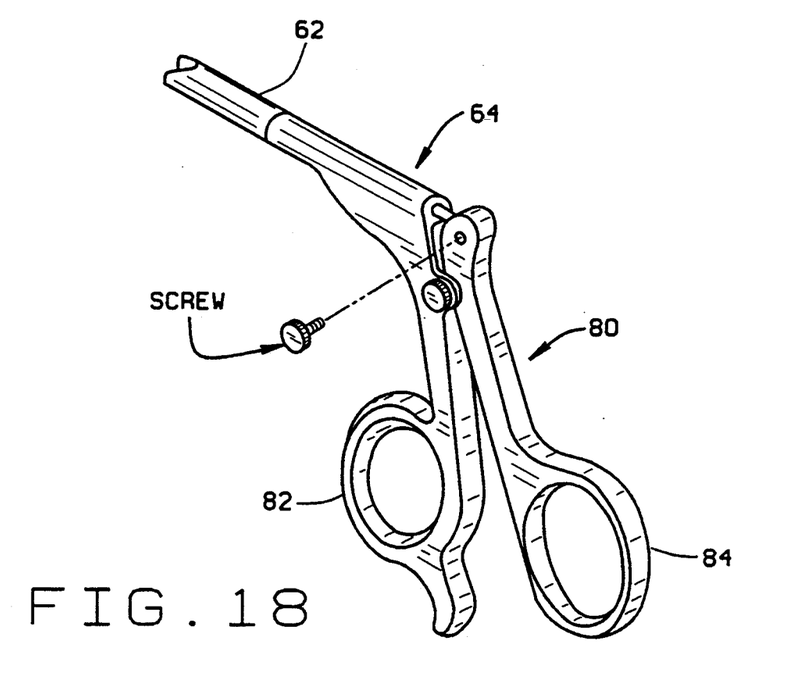
FIG. 18 is a perspective view of a scissors-style grip for the handle.
Figure 19:
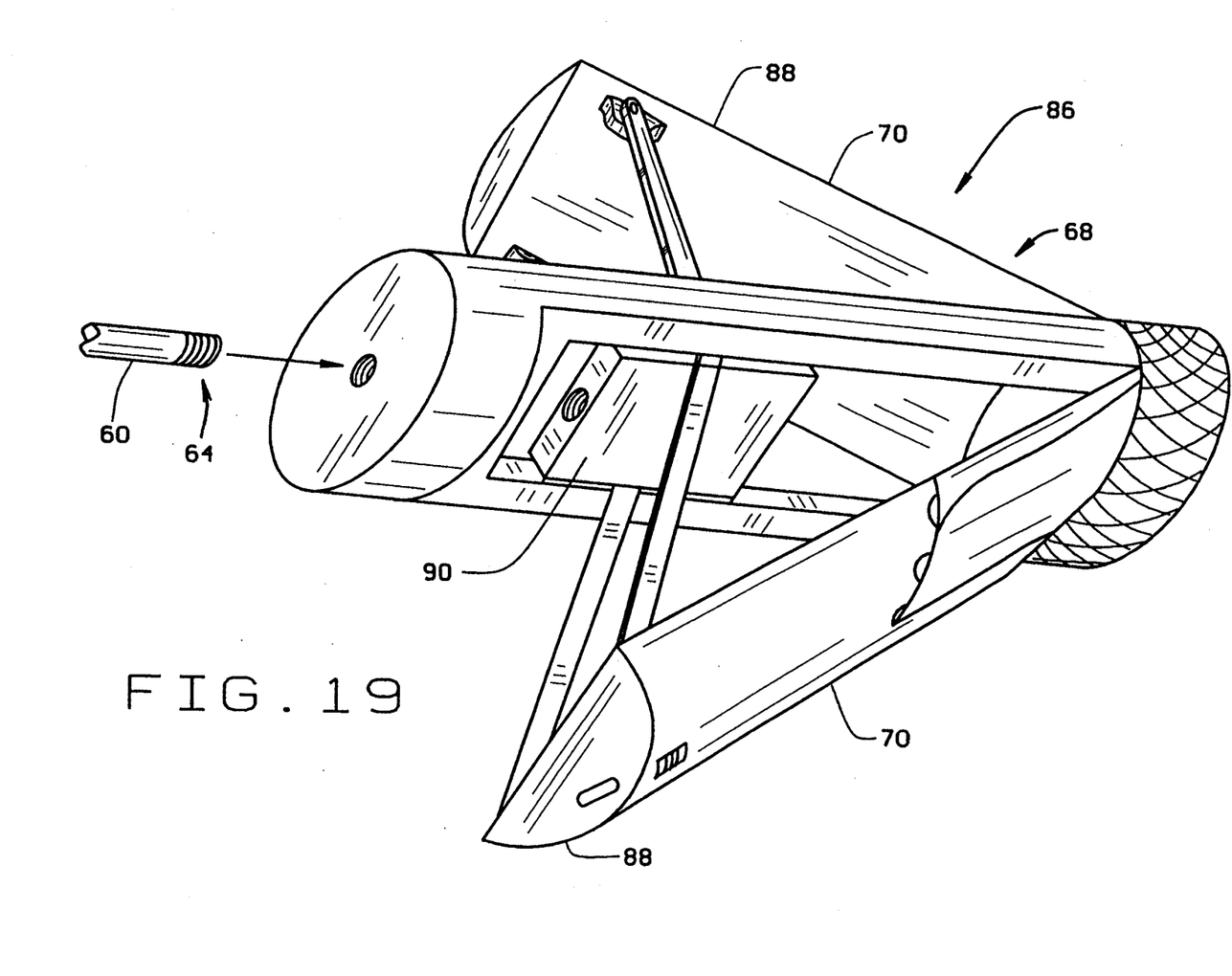
FIG. 19 is a perspective view of a cylindrical-style grip for the handle.

The proximal end of the handle 62 may have a grip 80 with a scissors configuration for operating the actuators 74 in the handle 62, as shown in FIG. 18. The grip 80 includes a stationery finger ring 82 for stabilizing the device, and a movable finger ring 84, operatively connected to the actuator 74, to move the actuator. However, the handle preferably has a generally cylindrical grip 86, as shown in FIG. 19, so that the surgeon can grasp the grip in any orientation. The cylindrical grip preferably has hinged levers 88 for operating the actuators, and a resilient safety mechanism for preventing the levers from over-operating the actuators. The movement of the levers 88 causes a block 90 to slide proximally and distally inside the grip 86. The actuator 74 is connected to the block 90, for example with mating threads, so movement of the block moves the actuator.

During the surgery, the surgeon can detach one surgical instrument head 24 from a handle 62, and attach a different surgical instrument head on the handle. For example, the surgeon might remove a surgical instrument head adapted for cutting, and replace it with a surgical instrument head for stapling or suturing. A surgical instrument head for applying biocompatible adhesives, such as fibrin-based adhesives, can be provided for closing surgical wounds with the use of sutures or staples.

When the surgery is complete, the surgical instrument heads 24 are detached from the distal ends 66 of the handles 62 to which they were attached. The surgical instrument heads are then exported through the cannula 22 that extends through the primary incision 20, preferably in their protective tray 40 or their tool holder 46. The handles 62 are simply withdrawn through their secondary incisions 58.

In addition to surgical instrument heads 24, surgical hardware can also be imported through the cannula 22 extending through the primary incision 20. For example, surgical clamps and staples or lenses for viewing or focusing optical energy can be imported through the primary incision .for use during the surgery. These clamps and staples can be installed using the surgical instrument heads 24 that were also imported through the cannula 22 extending through the primary incision 20.

The primary incision can be closed in a conventional manner, for example with a suture. In most cases the secondary incisions will be sufficiently small that no sutures are necessary.

OPERATION

According to the method of performing minimally invasive surgery according to this invention, a primary incision 20 is made through the umbilicus U of the body B of the patient, and a cannula 22 is installed. The patient's abdomen is inflated with carbon dioxide to provide a work space. Alternatively, a mechanical lifter can be used to rase the abdominal wall and provide a working space inside the body. A set of surgical instrument heads 24 is imported through the cannula 22 in a tray 40 or in a tool holder 46.

One or more secondary incisions 48 are made in the patient's body B for the introduction of handles 62. The shaft 60 of the handle 62 is preferably enclosed in a protective sleeve or sheath 72 so that movement of the handle 62 does not disturb the tissue surrounding the incisions. The distal end 66 of the handle 62 is manipulated to the appropriate sleeve 44 of the tray 40, or to the appropriate socket 50 of the tool holder 46. The surgical instrument head is attached to the distal end of the handle, for example by rotating the handle to thread the distal end 66 of the handle 62 into the surgical instrument head 24. The actuator 74 of the handle 62 can be actuated to manipulate the surgical instrument head while it is still in the socket 50, to confirm that the head is properly attached to the handle. The windows 52 in the holder 46 allows the surgeon to see whether the actuator is properly operating the surgical instrument head.

The surgical instrument head 24 is then withdrawn from the sleeve 44 or socket 50, whereupon the surgical instrument head can be used to conduct the surgery. When the surgeon is finished with a particular surgical instrument head, then the surgeon manipulates the surgical instrument head back into a sleeve 44 on the tray 40 or into a socket 50 in the tool holder 46. The surgeon detaches the surgical instrument head from the handle, for example by unscrewing it, and can then attach another surgical instrument head to the handle, if desired.

When the surgery is completed, the surgeon removes the surgical instrument heads from the handles, installing them on the sleeves 44 on the tray 40 or in the sockets 50 in the holder 46. The surgical instrument heads can then be exported through the cannula 22 secure in their respective trays 40 or tool holders 46. The surgical instrument heads are protected in their trays 40 or tool holders 46, reducing the risk of damage to the head, and allowing them to be conveniently transported for refurbishing so that they can be reused. Of course, the heads could simply be disposed of after use. The handles can simply be withdrawn from the secondary incisions 48. The handles can also be refurbished or they can simply be disposed of. The primary incision 20 is closed, for example with sutures. The secondary incisions are typically small enough that no suturing is necessary. The small incisions cause less trauma to the patient, and heal more quickly with minimal scarring. The small size of the incisions also make the method particularly suitable for pediatric surgeries, and even permit access to the thoracic cavity through the rib cage.

The surgical instruments of this invention are smaller, easier to handle, provide better access to the surgical site and better control. The instruments can be made much lighter, making them easier for the surgeon to grasp and manipulate, less fatiguing, and providing better sensory feed back. The surgical method makes laparoscopic surgery available for more procedures. The reduction in incision six reduces the risk of infection, reduces post operative complications, and reduces scarring. For the patient this can mean less pain, faster recovery, and shorter hospital stays.

What is claimed is:

1. A method of conducting minimally invasive surgery comprising the steps of:
   making a primary incision;
   importing at least one surgical instrument head, having a cross-section, through the primary incision;
   making at least one secondary incision, smaller than the primary incision and smaller than the smallest cross-section dimension of the surgical instrument head, each secondary section for receiving a handle having a distal end for mounting a surgical instrument head;
   extending the distal end of a handle through a said secondary incision;
   attaching a said surgical instrument head to the distal end of the handle inside the body;
   manipulating the surgical instrument head with the handle to which it is attached;
   detaching the surgical instrument head from the handle;
   removing the surgical instrument head through the primary incision; and
   withdrawing the distal end of the handle from the secondary incision.

2. The method of conducting surgery according to claim 1 wherein the handle provides pneumatic pressure to the surgical instrument head to which it is attached.

3. The method of conducting surgery according to claim 1 wherein the handle provides hydraulic pressure to the surgical instrument head to which it is attached.

4. The method of conducting surgery according to claim 1 wherein the handle provides electric power to the surgical instrument head to which it is attached.

5. The method of conducting surgery according to claim 1 wherein at the handle is inserted through the secondary incision so as to extend between the ribs of the subject so that the surgical instrument head can access the thorax.

6. The method of conducting surgery according to claim 1 wherein a plurality of surgical instrument heads are imported through the primary incision.

7. The method of conducting surgery according to claim 6 wherein of surgical instrument head on of handle is removed during the course of the surgery and replaced with a different surgical instrument head adapted for a different purpose.

8. The method of conducting surgery according to claim 1 wherein the primary incision is made through the umbilicus.

9. The method of conducting surgery according to claim 1 wherein the handle includes a mechanical handle for operating the surgical instrument head attached to the handle.

10. The method of conducting surgery according to claim 1 wherein the secondary incision is made from the inside of the patient.

11. A method of conducting minimally invasive surgery with an instrument comprising a surgical instrument head, having a cross-sectional area, and a handle, of smaller cross-sectional area than the surgical instrument head, the handle having a distal end to which the surgical instrument head can be attached, the method comprising:
   importing the surgical instrument head through a first incision;
   extending the distal end of the handle through a second incision that is smaller than the first incision and smaller than the smallest cross-sectional area of the surgical instrument head;
   attaching the surgical instrument head to the distal end of the handle inside the subject;
   manipulating the surgical instrument head with the handle;
   removing the surgical instrument head from the handle;
   removing the surgical instrument head from the subject; and withdrawing the distal end of the handle from the second incision.

12. The method of conducting surgery according to claim 11 wherein the handle provides pneumatic pressure to the surgical instrument head to which it is attached.

13. The method of conducting surgery according to claim 11 wherein the handle provides hydraulic pressure to the surgical instrument head to which it is attached.

14. The method of conducting surgery according to claim 11 wherein the handle provides electric power to the surgical instrument head to which it is attached.

15. The method of conducting surgery according to claim 11 wherein the handle is inserted through the secondary incision so as to extend between the ribs of the subject so that the surgical instrument head can access the thorax.

16. The method of conducting surgery according to claim 11 wherein a plurality of surgical instrument heads are imported through the first incision.

17. The method of conducting surgery according to claim 16 wherein a surgical instrument head on a handle is removed during the course of the surgery and replaced with a different surgical instrument head adapted for a different purpose.

18. The method of conducting surgery according to claim 11 wherein the first incision is made through the umbilicus.

19. The method of conducting surgery according to claim 11 wherein the handle includes a mechanical actuator for operating the surgical instrument head attached to the handle.

20. A method of assembling a surgical instrument comprising a surgical instrument head, having a cross-sectional area, and a handle having a distal end for mounting the surgical instrument head, the method comprising the steps of importing the surgical instrument head into the body of a patient through a primary incision made therein; introducing the distal end of the handle through a secondary incision that is smaller than the primary incision and the cross-sectional dimension of the surgical instrument head, and removably attaching the surgical instrument head to the distal end of the handle inside the patient's body.

* * * * *